United States Patent
Rice

(10) Patent No.: US 7,812,207 B2
(45) Date of Patent: Oct. 12, 2010

(54) MEMBRANE SEPARATION PROCESSES AND SYSTEMS FOR ENHANCED PERMEANT RECOVERY

(75) Inventor: Lynn H. Rice, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 598 days.

(21) Appl. No.: 11/851,577

(22) Filed: Sep. 7, 2007

(65) Prior Publication Data

US 2009/0069619 A1 Mar. 12, 2009

(51) Int. Cl.
*C07C 7/144* (2006.01)

(52) U.S. Cl. ............................ 585/818; 585/819

(58) Field of Classification Search ............ 585/818, 585/819
See application file for complete search history.

(56) References Cited

U.S. PATENT DOCUMENTS

| | | | |
|---|---|---|---|
| 3,043,891 A * | 7/1962 | Stuckey | 585/818 |
| 4,717,784 A | 1/1988 | Stem et al. | 585/738 |
| 4,735,193 A | 4/1988 | Kulprathipanja et al. | 127/46.3 |
| 4,740,219 A | 4/1988 | Kulprathipanja et al. | 55/16 |
| 4,804,802 A | 2/1989 | Evans et al. | 585/734 |
| 4,804,803 A | 2/1989 | Schmidt et al. | 585/748 |
| 4,925,459 A | 5/1990 | Rojey et al. | 155/16 |
| 4,925,562 A | 5/1990 | Te Hennepe et al. | 210/500.25 |
| 5,036,035 A | 7/1991 | Baba et al. | 502/221 |
| 5,069,794 A | 12/1991 | Haag et al. | 210/650 |
| 5,127,925 A | 7/1992 | Kulprathipanja et al. | 55/16 |
| 5,146,037 A | 9/1992 | Zarchy et al. | 585/738 |
| 5,326,296 A | 7/1994 | De Jesus | 441/60 |
| 5,430,224 A * | 7/1995 | Schucker | 585/818 |
| 5,705,730 A | 1/1998 | Zarchy et al. | 585/738 |
| 5,769,927 A * | 6/1998 | Gottschlich et al. | 95/39 |
| 5,922,639 A | 7/1999 | Alario et al. | 502/230 |
| 5,968,366 A | 10/1999 | Deckman et al. | 210/651 |
| 6,001,241 A | 12/1999 | Gosling et al. | 208/65 |
| 6,013,173 A | 1/2000 | Bogdan | 208/139 |
| 6,036,845 A | 3/2000 | Funk et al. | 208/65 |
| 6,090,289 A | 7/2000 | Verduijn et al. | 210/644 |
| 6,156,950 A | 12/2000 | Ragil et al. | 585/802 |
| 6,214,764 B1 | 4/2001 | Gillespie | 502/230 |
| 6,248,682 B1 | 6/2001 | Thompson et al. | 502/4 |

(Continued)

FOREIGN PATENT DOCUMENTS

EP 0 666 109 A1 1/1995

(Continued)

OTHER PUBLICATIONS

Separation of Normal Paraffins from Isoparaffins presented by I. A. Reddock, et al, at The Eleventh Australian Conference on Chemical Engineering, Brisbane, Sep. 4-7, 1983.

(Continued)

*Primary Examiner*—Tam M Nguyen
(74) *Attorney, Agent, or Firm*—Maryann Maas

(57) ABSTRACT

Membrane separation processes and systems are disclosed that pass a portion of the feed (102) to the permeate side of the membrane (104) to reduce membrane surface area and thus provide economically attractive processes and systems for treating large volume refinery and chemical process streams.

5 Claims, 1 Drawing Sheet

U.S. PATENT DOCUMENTS

| | | | | |
|---|---|---|---|---|
| 6,281,405 B1 * | 8/2001 | Davis et al. | ................ | 585/719 |
| 6,338,791 B1 | 1/2002 | Ragil et al. | .................. | 208/63 |
| 6,380,452 B1 * | 4/2002 | Davis et al. | ................ | 585/818 |
| 6,407,301 B1 | 6/2002 | Foley et al. | ................ | 585/650 |
| 6,503,295 B1 | 1/2003 | Koros et al. | .................... | 95/51 |
| 6,818,333 B2 | 11/2004 | Chau et al. | ................ | 428/702 |
| 6,818,589 B1 | 11/2004 | Gillespie | .................. | 502/326 |
| 2003/0196931 A1 | 10/2003 | Houzvicka et al. | ............ | 208/65 |
| 2005/0283037 A1 | 12/2005 | Briot et al. | ................ | 585/535 |

FOREIGN PATENT DOCUMENTS

| | | |
|---|---|---|
| WO | WO 2005/012397 A2 | 7/2004 |
| WO | WO 2005/049766 A1 | 6/2005 |

OTHER PUBLICATIONS

McKeown, et al., Chem, Commun., 2780 (2002).
McKeown, et al.,, Chem. Eur. J., 11:2610 (2005).
Budd, et al., J. Mater. Chem., 13:2721 (2003).
Budd, et al., Adv. Mater., 16:456 (2004).
Budd, et al., Chem Commun., 230 (2004).

* cited by examiner

MEMBRANE SEPARATION PROCESSES AND SYSTEMS FOR ENHANCED PERMEANT RECOVERY

BACKGROUND OF THE INVENTION

This invention pertains to membrane separation processes and systems that provide for increased recovery of the sought permeant. For purposes herein, the permeant is the component for which the membrane is intended to selectively permeate. Thus the fluid feed and the permeate fraction would contain permeant and the retentate fraction may contain permeant. The retentant is the component of the feed which is intended to be selectively rejected by the membrane. A fluid feed may contain two or more components and thus there may be two or more retentant and two or more permeants. Except as otherwise stated, where more than one permeant exist, the permeant shall mean the most desired component in the permeate fraction, e.g., normal paraffins where the feed is a naphtha fraction. Similarly, where more than one retentant exist, the retentant shall mean the most desired component in the retentate fraction, e.g., branched paraffins where the feed is an effluent from an isomerization of a $C_5$ and $C_6$ feedstock.

Membranes have been proposed as an alternative separation unit operation. The membrane separations have had limited commercial success in displacing alternative separation unit operations such as distillation, selective sorption, liquefaction and crystallization. In some instances, the capital cost of membranes for a given recovery of permeant is a significant deterrent from the use of a membrane separator, particularly for large-scale commercial processes. For example, refineries process large volumes of hydrocarbon feeds including the difficult separations of closely boiling components such as isomers and aromatic and aliphatic compounds of similar molecular weights. Nevertheless, distillation and sorption separation processes are still the primary processes for these difficult separations.

One of the disadvantages to the use of membrane separation processes for refinery applications is that extremely large membrane surface areas would have to be provided in order to achieve the sought separations. Many membranes that have been proposed for refinery and chemical process uses have been made with relatively thick barrier layers so as to assure that the sought separation can be achieved. See, for instance, U.S. Pat. No. 5,069,794 disclosing microporous membranes containing crystalline molecular sieve material; and U.S. Pat. No. 6,090,289, disclosing a layered composite containing molecular sieve that could be used as a membrane. The selectivities of the membranes can be quite high. For example, U.S. Pat. No. 6,818,333 discloses thin zeolite membranes that are said to have a permeability of n-butane of at least $6 \cdot 10^{-7}$ mol/m$^2$·s·Pa and a selectivity of at least 250 of n-butane to isobutane. Recently, Bourney, et al., in WO 2005/049766 disclose a process for producing high octane gasoline using a membrane to remove, inter alia, n-pentane from an isomerized stream derived from the overhead of a deisohexanizer. In a computer simulation based upon the use of an MFI on alumina membrane, example 1 of the publication indicates that 5000 square meters of membrane surface area is required to remove 95 mass percent of n-pentane from the overhead from a deisohexanizer distillation column. At the flow rate of feed to the permeator (75000 kg/hr. having 20.6 mass percent n-pentane), the flux of n-pentane used in the simulation appears to be in the order of 0.01 gram moles/m$^2$·s at 300° C.

Thus, the costs for commercially implementing such a membrane separation system render it not competitive with respect to an adsorption separation system even if the entire naphtha stream were treated to remove contaminants potentially deleterious to the sorbent.

Additionally, membrane separators have fixed surface areas and to provide a product of constant purity over a range of feed rates and feed compositions, changes in the driving force, e.g., partial pressure or concentration gradients, may need to be made. Similarly, if a membrane becomes fouled resulting in the loss of permeance, the recovery of permeant will decrease unless changes in driving force are made to compensate for such loss.

Alternatives to, for instance, distillation systems for separations are sought due at least in part to the high energy consumption of the distillation process. Selective sorption processes can be more energy efficient than distillations but often involve more capital expense than a distillation system. Membrane separation systems generally offer an energy efficient separation as the driving force for the permeation is typically a differential in partial pressure or concentration.

Accordingly, a need exists to develop membrane separation systems that are an economically attractive alternative to conventional separation systems, especially where large volume streams must be treated. Membrane separation systems are also desired that can provide constant product purity over a wide range of feed rates and compositions without the complexities of changing the driving force for the separation.

SUMMARY OF THE INVENTION

In accordance with this invention, processes and systems are provided that enhance the economic viability of membranes for refinery and chemical process separations and permit flexibility in achieving a desired recovery of permeant without resort to having to change driving forces for the permeation. Accordingly, changes in, for instance, feed composition and membrane condition such as fouling, can be readily accommodated to provide constant permeate recovery. In preferred embodiments, the processes and systems of the invention enable the concentration of the retentant in the retentate to be substantially constant even though the volume of permeant changes.

The membrane processes and systems of this invention are particularly advantageous in refining and chemical processes where the purity of the permeant in the permeate is not critical. One such application is in isomerizations, especially of alkanes and alkenes of 4 to 30 carbon atoms such as butane isomerization and isomerization of light naphtha feeds to make higher octane fuels, aromatics such as xylenes, and the like. Another example is optimizing a feed to a reactor such as treating a feedstock containing normal and branched and cyclic hydrocarbons to provide a stream enriched in normal hydrocarbons for steam cracking and a stream depleted in normal hydrocarbons for reforming. Even limited selectivity of separation can assist distillations, either by effecting a portion of the separation or in breaking azeotropes and can assist other reactions, e.g., by removing at least a portion of the desired product to prevent it from further reacting such as in alkylation reactions.

In one broad aspect of the invention, the processes comprise:

a. passing a fluid feed containing at least two components to be separated to a retentate side of a selective permeation membrane having a retentate side and opposing permeate side, b. maintaining a driving force across the membrane to effect separation of at least one of said components by permeation through the membrane to provide a permeate fraction on the permeate side of the membrane, c. withdrawing a portion, preferably at least 5, say, 5 to 40, mass percent of the fluid feed for admixing with at least a portion of said permeate fraction without said withdrawn portion passing through said membrane, and d. withdrawing a retentate fraction from the retentate side of the membrane, said retentate fraction having a greater concentration of the other of said at least two components than said feed.

In another aspect, the processes of the invention comprise:

a. passing a fluid feed containing at least two components to be separated to a retentate side of a selective permeation membrane having a retentate side and opposing permeate side, b. maintaining a driving force across the membrane to effect separation of at least one of said components by permeation through the membrane to provide a permeate fraction on the permeate side of the membrane, c. withdrawing a retentate fraction from the retentate side of the membrane, said retentate fraction having a greater concentration of the other of said at least two components than said feed, and d. withdrawing a sufficient portion of the fluid feed for admixing with at least a portion of said permeate fraction without said withdrawn portion passing through said membrane to provide a desired concentration of the other of said at least two components in the retentate fraction.

One broad aspect of the membrane separation systems of this invention comprise:

a. a membrane separator having selective permeation membrane therein adapted to define a retentate side and a permeate side, b. at least one feed conduit adapted to provide a fluid feed containing at least two components to be separated to the retentate side, c. at least one by-pass conduit adapted remove a portion of the fluid feed such that it does not pass through said membrane, d. at least one conduit adapted to withdraw from the retentate side a retentate fraction, and e. at least one conduit adapted to withdraw from the permeate side a permeate fraction, in which conduit (c) is in fluid communication with at least a portion of the permeate fraction.

Another aspect of the systems of this invention comprise:

a. a membrane separator (104) having selective permeation membrane therein adapted to define a retentate side and a permeate side, b. at least one feed conduit (102) adapted to provide a fluid feed containing at least two components to be separated to the retentate side, c. at least one by-pass conduit (110) adapted remove a portion of the fluid feed such that it does not pass through said membrane, d. at least one conduit (108) adapted to withdraw from the retentate side a retentate fraction, and e. at least one conduit (106) adapted to withdraw from the permeate side a permeate fraction, in which conduit (110) is in fluid communication with at least a portion of the permeate fraction.

DETAILED DESCRIPTION OF THE INVENTION

Figure 1:
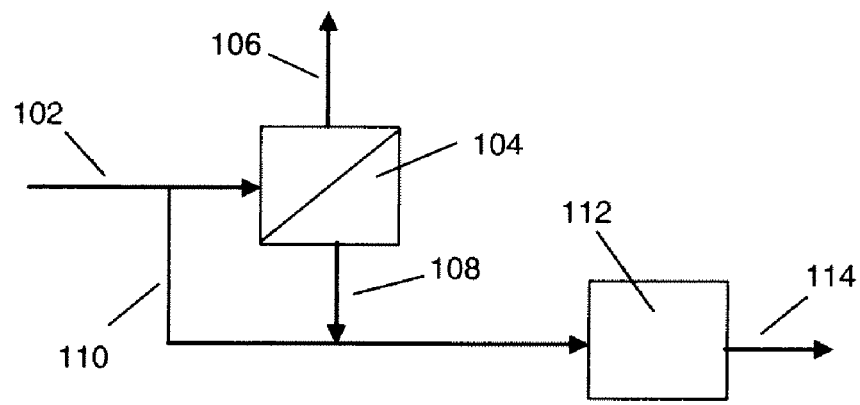
FIG. 1 is a schematic depiction of processes and systems in accordance with this invention.

The processes and systems of this invention can be used with various fluid feeds, especially those in refinery and chemical facilities, where purity of the permeant in the permeate fraction is not critical. In general, such applications will involve a recycle reaction process where unreacted component is recycled to the reaction zone or a pretreatment process where the fluid feeds are enriched or depleted in a component to facilitate a reaction or another separation process.

Exemplary applications include the separation of normal paraffins from branched paraffins and cyclic paraffins and aromatics for recycle to isomerization reactors; separation of olefins from paraffins or oxygenated compounds such as alcohols, ethers, carboxylic acids and esters or halogen-containing compounds such as alkylchlorides, and the like; separation of normal paraffins from naphtha feedstocks to provide enhanced feeds for reforming and for cracking; separation of benzene and aliphatics from alkylbenzene for recycle in benzene alkylation processes; and separation of normal butane from isobutane-containing feed for butane dehydrogenation.

The fluid feed for the processes of this invention may be liquid or gaseous or mixed phase. The permeate fraction may also be liquid or gaseous or mixed phase. A sweep fluid may be provided on the permeate side of the membrane to enhance the driving force for the permeation by reducing the permeant partial pressure or concentration on the permeate side of the membrane.

The membranes may be in any suitable form such as hollow fibers, sheets, and the like which can be assembled in a separator unit such as bundled hollow fibers or flat plate or spiral wound sheet membranes. The physical design of the membranes should enable, when assembled in the separator unit, sufficient pressure drop across the membrane to provide desirable flux. For hollow fiber membranes, the high pressure side (retentate side) is usually at the outside of the hollow fiber. The flow of the permeate may be co-current, counter-current or cross-current with respect to the flow of the fluid on the retentate side of the membrane.

Any suitable membrane may be used including, but not limited to diffusion and sieving, and may be constructed of inorganic, organic or composite materials. For diffusion membranes, the driving force is the differential in partial pressures or concentration between the retentate and the permeate sides. In sieving membranes, the absolute pressure drop becomes a significant component of the driving force independent of partial pressures or concentrations.

A preferred type of membrane is composite membranes that use molecular sieve as an adsorbing layer to effect the separation. See, for instance, U.S. Pat. No. 6,407,301. U.S. Pat. No. 5,069,794 discloses microporous membranes containing crystalline molecular sieve material. See also, U.S. Pat. No. 6,090,289, disclosing a layered composite containing molecular sieve that could be used as a membrane. US Publication 2003/0196931 discloses a two-stage isomerization process for up-grading hydrocarbon feeds of 4 to 12 carbon atoms. The use of zeolite membranes is suggested as a suitable technique for separating normal molecules. See, for instance, paragraphs 0008 and 0032. U.S. Pat. No. 6,818,333 discloses thin zeolite membranes that are said to have a permeability of n-butane of at least $6 \cdot 10^{-7}$ mol/m$^2$·s·Pa and a selectivity of at least 250 of n-butane to isobutane. Sieving membranes may be of various types, for instance, molecular sieves, pore-containing ceramic, metal, polymeric or carbon membranes, or composite membranes having a highly porous polymeric, metallic, molecular sieve, ceramic or carbon support with a thin sieving layer, e.g., molecular sieve or carbon.

In accordance with this invention, a portion of the fluid feed by-passes permeating the membrane and is admixed with at least a portion of the permeate fraction. The amount of by-passed will depend upon the separation efficiency of the membrane, the amount of the retentant desired to be provided in the retentate fraction and its purity, and the purity of the permeant in the permeate fraction. In the processes of this invention, at least 5 up to 40 mass percent of the feed by-passes the membrane. In applications where the purity of the permeant in the permeate fraction is not critical, greater amounts, say, 10 to 40 mass percent of the feed may be by-passed. In some instances, the amount by-passed will be that assured that at least 80, preferably at least 90, mass percent of permeant in the feed is contained in the permeate fraction through a combination of permeation and by-pass. The retentate fraction typically contains at least 60 mass percent up to 95 mass percent of the retentant contained in the feed.

The by-pass of the processes of this invention also permits the retentate fraction to have a relatively low concentration of permeant. For instance, the retentate fraction may contain less than 20, preferably less than 10, and often less than 5, mass percent permeant contained in the feed.

The amount of membrane surface area that is provided will depend upon the amount of the by-pass, the flux rate of the permeant through the membrane and the desired purity of retentant in the retentate fraction. As can be readily appreciated, a high purity retentate fraction can be provided with less membrane surface area than would be required without the by-pass, all other things remaining the same. Also, for a given recovery of permeant in the permeate fraction, less membrane surface area would be required than without a by-pass, all other things remaining the same. In preferred processes and systems according to this invention, the required membrane surface area is at least 25 percent less than that to provide, in the absence of the by-pass, the same amount of permeant in the retentate fraction including the by-pass, and the same concentration of permeant in the retentate fraction, all else being equal.

The fraction of the feed for the by-pass can be taken at any suitable point or points. For instance, the portion to be by-passed may be withdrawn from the feed prior to introduction into a vessel containing the membrane. Alternatively, it may be withdrawn in the vessel. Where more than one membrane stage is used, a portion may be withdrawn between stages. Preferably, the portion withdrawn is taken prior to contact of the feed with the membrane since the feed has the greatest concentration of permeant at that point.

The by-passed portion of the feed may be passed to the permeate side of the membrane or admixed with one or more effluent streams containing permeate fraction.

DETAILED DESCRIPTION OF THE DRAWINGS

With reference to FIG. 1, a fluid feed stream containing retentant and permeant is directed via line 102 to membrane separator 104. A retentate fraction is withdrawn from membrane separator 104 via line 106 and is enriched in retentant as compared to the feed. A permeate fraction is withdrawn from membrane separator via line 108 and is combined with a portion of the feed withdrawn from line 102 via line 110. The combined fluid is passed to unit operation 112 to provide a product stream 114.

If unit operation 112 is an isomerization unit and the permeant is a normal paraffin, the fluid in line 114 would contain branched paraffins which could be used for a gasoline pool or as a feed to another unit operation. If desired, at least a portion of the product in line 113 could be recycled to line 102 for separation in separator 104 with the retentate fraction containing the sought branched paraffins and normal paraffins being recovered in the permeate fraction for recycle to the isomerization unit.

Figure 2:
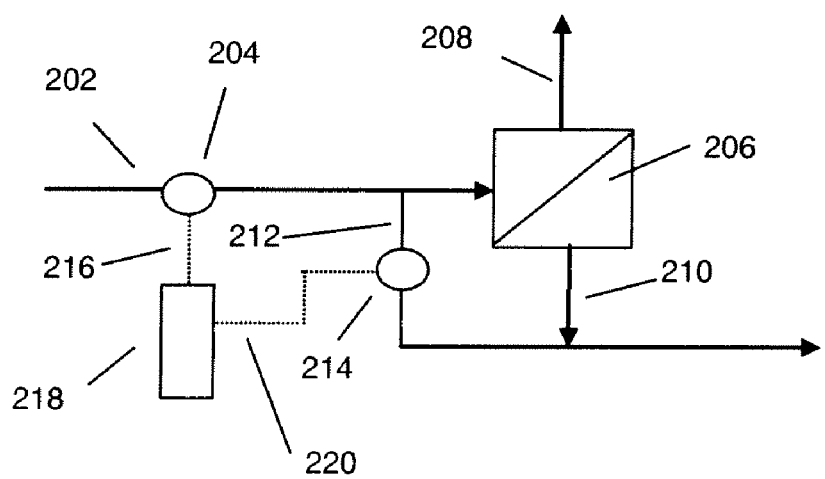
FIG. 2 is a schematic depiction of a control system in accordance with this invention.

In FIG. 2, a feed is supplied via line 202 to a membrane separation system. Sensor 204 is in communication with the fluid in conduit 202. Sensor 204 may be one or more sensors and adapted to determine feed flow rate such as conventional flow meters and/or adapted to determine the concentration of one or more components in the feed, including the feed composition such as gas or liquid chromatography, IR spectrometers, nuclear magnetic spectrometry, mass spectrometry, and the like. Sensor 204 also generates a signal responsive to the determination. A portion of the feed is directed to membrane separator 206. A retentate fraction is withdrawn via conduit 208 and a permeate fraction is withdrawn via line 210.

Another portion of the feed is withdrawn from line 202 via line 212 have flow control valve 214. As shown, sensor 204 is in communication with central processing unit 218 via line 216. The central processing unit receives the signal regarding the condition of the feed from sensor 204 and instructs valve 214 as to the amount of feed to by-pass membrane separator 206 in order to maintain the sought purity of retentant in the retentate fraction. Line 220 carries the instruction. While valve 214 is shown as being positioned on line 212, it is apparent that the rate of flow in line 212 can be effected by a splitter valve at the junction of lines 202 and 212 or by a valve on line 202.

The invention claimed is:

1. A membrane separation process comprising:
    a. passing a fluid feed containing at least two components to be separated to a retentate side of a selective permeation membrane having a retentate side and opposing permeate side,
    b. maintaining a driving force across the membrane to effect separation of at least one of said components by permeation through the membrane to provide a permeate fraction on the permeate side of the membrane,
    c. withdrawing at least 5 mass percent of the fluid feed for admixing with at least a portion of said permeate fraction without said withdrawn portion passing through said membrane, and
    d. withdrawing a retentate fraction from the retentate side of the membrane, said retentate fraction having a greater concentration of the other of said at least two components than said feed.

2. The process of claim 1 wherein 5 to 40 mass percent of the fluid feed is withdrawn in step (c).

3. The process of claim 2 wherein at least 90 mass percent of the permeant in the feed is contained in the retentate fraction including the withdrawn fraction of step (c).

4. The process of claim 2 wherein the retentant fraction contains less than 10 mass percent of the permeant contained in the feed.

5. The process of claim 2 wherein the surface area of the membrane in step (a) is at least 25 percent less than that to provide, in the absence of step (c), the same amount of permeant in the retentate fraction including the withdrawn fraction of step (c), and the same concentration of permeant in the retentate fraction, all else being equal.

* * * * *